(12) United States Patent
Tanguay, Jr. et al.

(10) Patent No.: US 8,210,680 B2
(45) Date of Patent: Jul. 3, 2012

(54) OCULAR IMAGING SYSTEM

(75) Inventors: Armand R. Tanguay, Jr., Yorba Linda, CA (US); Mark S. Humayun, Glendale, CA (US)

(73) Assignees: University of Southern California, Los Angeles, CA (US); Doheny Eye Institute, Los Angeles, CA (US)

( * ) Notice: Subject to any disclaimer, the term of this patent is extended or adjusted under 35 U.S.C. 154(b) by 365 days.

(21) Appl. No.: 12/429,964

(22) Filed: Apr. 24, 2009

(65) Prior Publication Data

US 2010/0026957 A1     Feb. 4, 2010

Related U.S. Application Data

(60) Provisional application No. 61/048,180, filed on Apr. 26, 2008.

(51) Int. Cl.
*A61B 3/10*     (2006.01)

(52) U.S. Cl. ........................................ 351/205; 351/246

(58) Field of Classification Search .......... 351/205–206, 351/246
See application file for complete search history.

(56) References Cited

U.S. PATENT DOCUMENTS

| | | | |
|---|---|---|---|
| 5,115,124 A | | 5/1992 | Muto et al. |
| 5,570,698 A | | 11/1996 | Liang et al. |
| 5,956,125 A | * | 9/1999 | Rosse et al. ................... 351/221 |
| 5,993,001 A | | 11/1999 | Bursell et al. |
| 7,311,401 B2 | | 12/2007 | Goldfain et al. |
| 7,420,153 B2 | | 9/2008 | Palmer et al. |
| 7,448,753 B1 | * | 11/2008 | Chinnock ....................... 351/206 |
| 2008/0029708 A1 | | 2/2008 | Olsen et al. |

OTHER PUBLICATIONS

International Search Report for PCT Application Serial No. PCT/US09/41723, mailed on Oct. 2, 2009.

* cited by examiner

*Primary Examiner* — James Greece
(74) *Attorney, Agent, or Firm* — McDermott Will & Emery LLP

(57) ABSTRACT

An imaging system for examining the interior structure of the eye at high-resolution under ambient light without the need for chemical dilation of the pupil.

27 Claims, 2 Drawing Sheets

OCULAR IMAGING SYSTEM

CROSS-REFERENCE TO RELATED APPLICATIONS

This application claims priority from provisional application 61/048,180, "Low Light Level Imaging System for Ophthalmological Examination", filed Apr. 26, 2008, which is hereby incorporated by reference in its entirety.

STATEMENT REGARDING FEDERALLY SPONSORED RESEARCH

This invention was made with government support under Grant Number NSF EEC-0310723, awarded by the National Science Foundation. The government has certain rights in the invention.

BACKGROUND

1. Field

The present disclosure relates generally to optical devices and instrumentation for ophthalmological examination.

2. General Background

Detailed images of internal structures of the retina allow detection of ocular pathology at an earlier, more treatable stage. Examinations to obtain such images are often not performed because the pupil naturally restricts the field of view, thereby limiting in turn the eye regions and structural detail apparent to the physician. Dilation of the pupil allows more light into the eye from either the ambient environment or an external light source, and also allows more light to be reflected from the eye through the enlarged aperture of the pupil.

Attempts to address this problem have taken several forms, many of which are cited in U.S. Pat. No. 7,311,401, which is hereby incorporated by reference in its entirety. Mydriasis, the drug-induced dilation of the pupil, allows sufficient light into the eye to permit detailed colored imaging of the retina, but necessitates extra time to induce dilation, and furthermore makes the patient's eyes painfully sensitive to light for hours afterward.

An alternative way of getting enough light into the eye is to use flashlamps, which emit high-intensity light. Flashlamps, however, cause patients discomfort, and according to recent studies, can damage retinal cells. In addition, flashlamp-based cameras are not amenable to extended observation, but are essentially "one shot" devices as pupil contraction occurs immediately following the flash, obviating further study.

A third approach is to use image intensifiers to make more efficient use of pupil-limited light fluxes. Image intensifiers, however, result in relatively low resolution monochrome images, thereby making detection of pathology difficult.

Thus a need exists for a way to obtain detailed, high-resolution color images of a patient's retina without use of mydriasis or light sources apart from ambient room light.

SUMMARY

The present disclosure addresses this need by providing an ocular imaging system that obviates the need for mydriasis or high-intensity light sources by allowing detailed examination of the retina with light levels that do not cause the pupils to constrict.

The ocular imaging system disclosed here includes an image sensor array that detects ambient light reflected from the patient's retina to produce an image of the patient's retina for the physician to examine.

DETAILED DESCRIPTION

Figure 1:
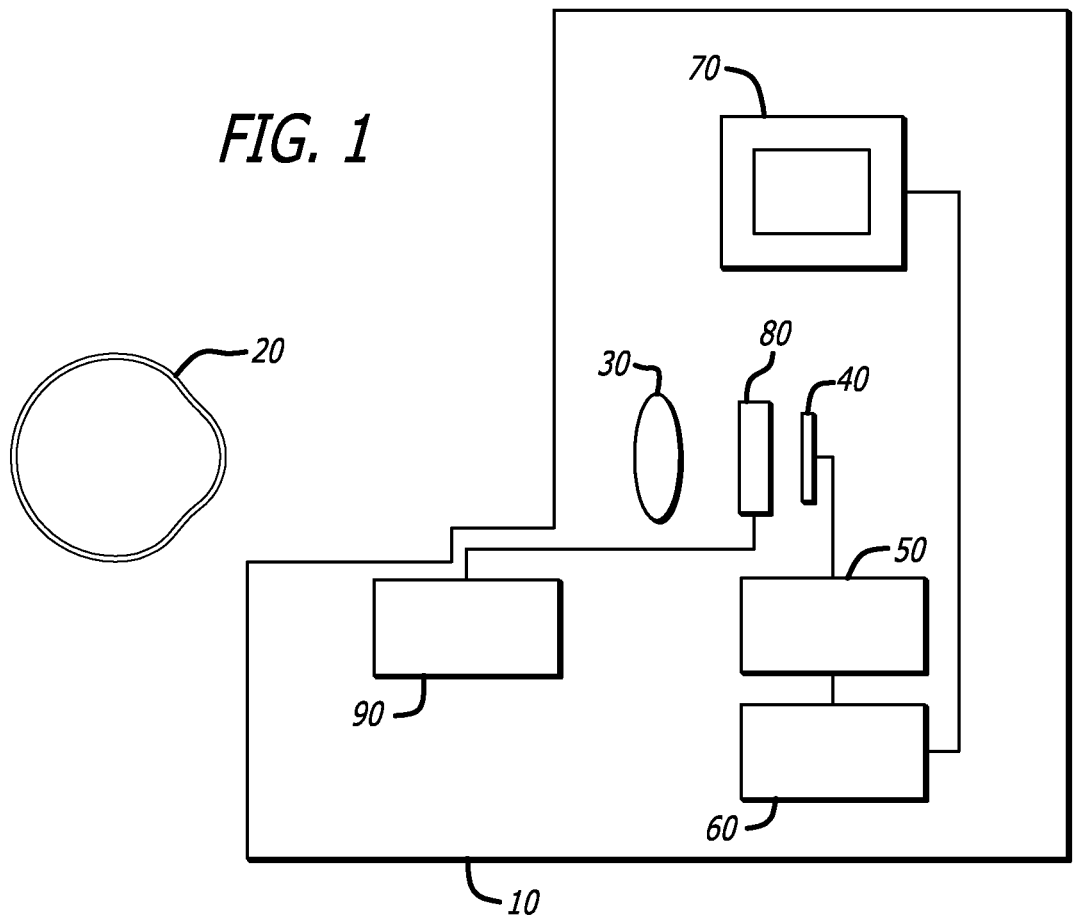
FIG. 1 depicts an exemplary ocular imaging system.

"Ambient light" as used here refers at illuminance levels between about 10 and about 100 lux.

"High-sensitivity" when applied to an image sensor array refers to an array that yields a measurable response to light of illuminance less than about 0.01 lux.

"Ambient light" as used here refers to illuminance levels between about 10 and about 100 lux.

"Low light" refers to light of illuminance levels less than about 10 lux.

"Imaging" refers to generation of a visual depiction of an object, whether or not that depiction is tangible, and includes both evanescent visual inspection and depictions.

Unless otherwise specified, other technical terms take the meanings specified in the McGraw-Hill Dictionary of Scientific and Technical Terms, $6^{th}$ edition.

Low-light monochrome viewing devices recently developed for military and law enforcement applications, as described for example in U.S. Pat. No. 7,420,153, which is hereby incorporated by reference in its entirety, have been adapted by the applicants to yield an ocular imaging system that provides high-resolution eye structure and retinal images under ambient light conditions that dilate the pupil physiologically, without the use of mydriasis or flashlamps. Furthermore, when used in conjunction with a tunable color filter, the system can provide images with veridical (true) or pseudocolor, as desired, thereby facilitating the detection of ocular pathology by the examining physician.

Specifically, this disclosure describes an ocular imaging system for imaging an eye, comprising a high-sensitivity, high-resolution image sensor array, with a sensitivity of at least about 0.1 lux, and preferably of at least about 0.01 lux, and more preferably of at least about 0.001 lux.

The system comprises a sensor array selected from the group consisting of CCD and CMOS devices, wherein the sensor array is preferably constructed of a material selected from the group consisting of silicon and silicon-germanium, and further comprises imaging optics disposed between the eye and the sensor array and adapted to form an image of the eye on the sensor array.

The imaging optics includes at least one element selected from the group consisting of a refractive lens, a gradient index lens, a diffractive lens, a diffractive optical element, and a variable focal length lens.

The system further comprises a fixed pattern or tunable color filter disposed between the sensor array and the eye for filtering the light, having a wavelength, that impinges on the sensor array. In the case of the tunable color filter, the filter is tuned by a voltage impressed upon the filter by a filter control circuit that controls the wavelength transmission profile of light passed by the filter, so that the wavelength transmission profile of the filter can be changed. The system also comprises an image processing circuit that combines signals obtained from the sensor array at two or more wavelength transmission profiles to yield an image. Additionally, the system comprises a communications circuit for transmitting the resulting image to a display device.

The disclosed system is used as a method of imaging an eye, wherein the imaging is performed at an ambient light level below about 500 lux, or preferably below about 200 lux, more preferably below about 100 lux, and still more preferably below about 50 lux. The method has application in diagnosing the health of an eye, through use of the system to form an image of the eye for examination for pathology or injury.

FIG. 1 illustrates an exemplary ocular imaging system 10. Light reflected from the interior of eye 20 impinges on imaging optics 30, which form an image on image sensor array 40. Imaging optics 30 may comprise such optical elements as a refractive lens (e.g., a lens with spherical or aspherical surfaces, or a gradient index (GRIN) lens), a diffractive lens, a diffractive optical element (DOE), or a variable focal length lens, selected as desired to vary the system focal length, magnification, aberration correction, resolution at the focal plane (at or near the image sensor array), and/or working distance (the distance between an optical element and the object being imaged). Imaging optics 30 are preferably designed to work in conjunction with any other optical elements, such as the corneal lens and crystalline lens, that may be present in the optical path between the interior of eye 20 and array 40.

Image sensor array 40 may be based upon silicon, silicon-germanium, complementary metal-oxide-semiconductors (CMOS), a charge-coupled device (CCD), or other arrays that exhibit high sensitivity toward light in the visible and/or infrared regions. If desired, image sensor array 40 may further comprise an anti-aliasing filter to reduce aliasing.

One example of a suitable sensor array, the Sony Super-HAD ICX638AKA color CCD array, has been primarily used for security applications. It incorporates a hole accumulation diode layer to minimize dark current, and high fill factor microlenses designed to focus the light within each pixel within the active area of the silicon CCD, eliminating loss due to low fill factor. In combination, these features promote high light sensitivity, thereby enabling imaging in low light level conditions.

Some choices for sensor array 40, such as Sony SuperHAD ICX638AKA color CCD array above, incorporate Bayer color filters, but others do not. Many examples exist of black and white (monochrome) image sensor arrays, such as incorporated in the Watec 902HB2 monochrome board camera, which has a sensitivity of 0.0003 lux when used with imaging optics operating at f/1.4.

The quantitative improvement in sensitivity conferred by these features provides a qualitative advance by enabling detailed ocular imaging under ambient light.

Sensor array control circuit 50 provides conditioned power for image sensor array 40, as well as signals to control operation of image sensor array 40, such as the frame rate, by methods well-known in the art. Circuit 50 may optionally also perform analog-to-digital conversion, as well as buffering of each frame of the readout image. Image processing circuit 60 provides image post-processing functions, such as color balancing, white balancing, brightness control, automatic gain control, and gamma correction, among others, in addition to pseudocoloring operations. Circuit 60 may also be configured to communicate data to display 70. Alternatively, the communications function may be implemented in a separate circuit (not shown).

If desired, tunable color filter 80 can be incorporated in the optical path between the eye and image sensor array 40, either before or after imaging optics 30. Suitable tunable color filters based on liquid crystals are available from CRi (Micro-Color, MacroColor, and VariSpec) but the choice of filter is not critical.

Tunable color filter control circuit 90 sends programming voltages to filter 80, which is voltage programmable to provide an optical bandpass tuned to a given central wavelength, or to several central wavelengths in succession. Circuit 90 thereby controls the wavelength transmission profile of filter 80, and also sets the dwell time (the amount of time that the tunable color filter is set to a particular wavelength) at each wavelength. This allows compensation for wavelength-dependent differences in the sensitivity of image sensor array 40, and in the optical transmission (throughput) of filter 80. Such compensation also allows for the re-balancing of the various color components to provide veridical color, thereby facilitating detection of subtle abnormalities and improving diagnostic sensitivity and specificity.

Alternatively, a set of thin film filters can be integrated into image sensor array 40, as is already known in the art for other sensor arrays.

The physical locations of circuits 50, 60, and 90 are not critical. Any or all of them may be incorporated in whole or in part within a housing enclosing system 10, or in a separate module, or as a plug-in board within an associated computer platform. Similarly, the location and precise nature of display 70 is not critical. Display 70 may, for example, be hand-held, head-mounted, free-standing, or attached to ocular imaging system 10. In the same vein, communications between circuit 60 and display 70 may take place either via wire or wirelessly, and the associated signals may be either analog or digital.

Figure 2:
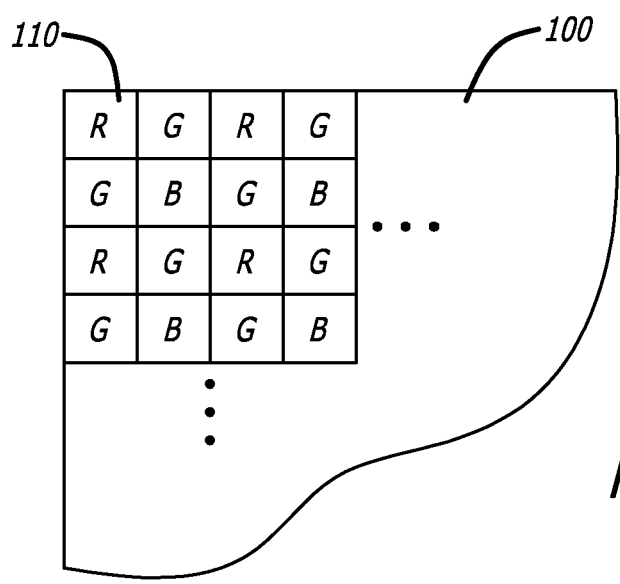
FIG. 2 shows an exemplary color filter pattern that may be incorporated in thin film form over the image sensor array to provide color images.

Image sensor array 40 may be monochromatic (or grey scale only), and a suitable color filter pattern (such as the Bayer pattern) may be added in the form of pixellated thin film coatings to form a color sensor. FIG. 2 shows an exemplary Bayer color filter pattern comprising an array of pixels 100 overlain with a grid of individual thin film coatings 110 to provide color differentiation within each associated group of nearest neighbor pixels. Interpolation algorithms can then be used to produce color coordinates for each region of the image. If desired, color filters modified to enhance the imaging of retinal and eye structures may be used in coatings 110 instead of common red, green, and blue filters (RGB).

Figure 3:
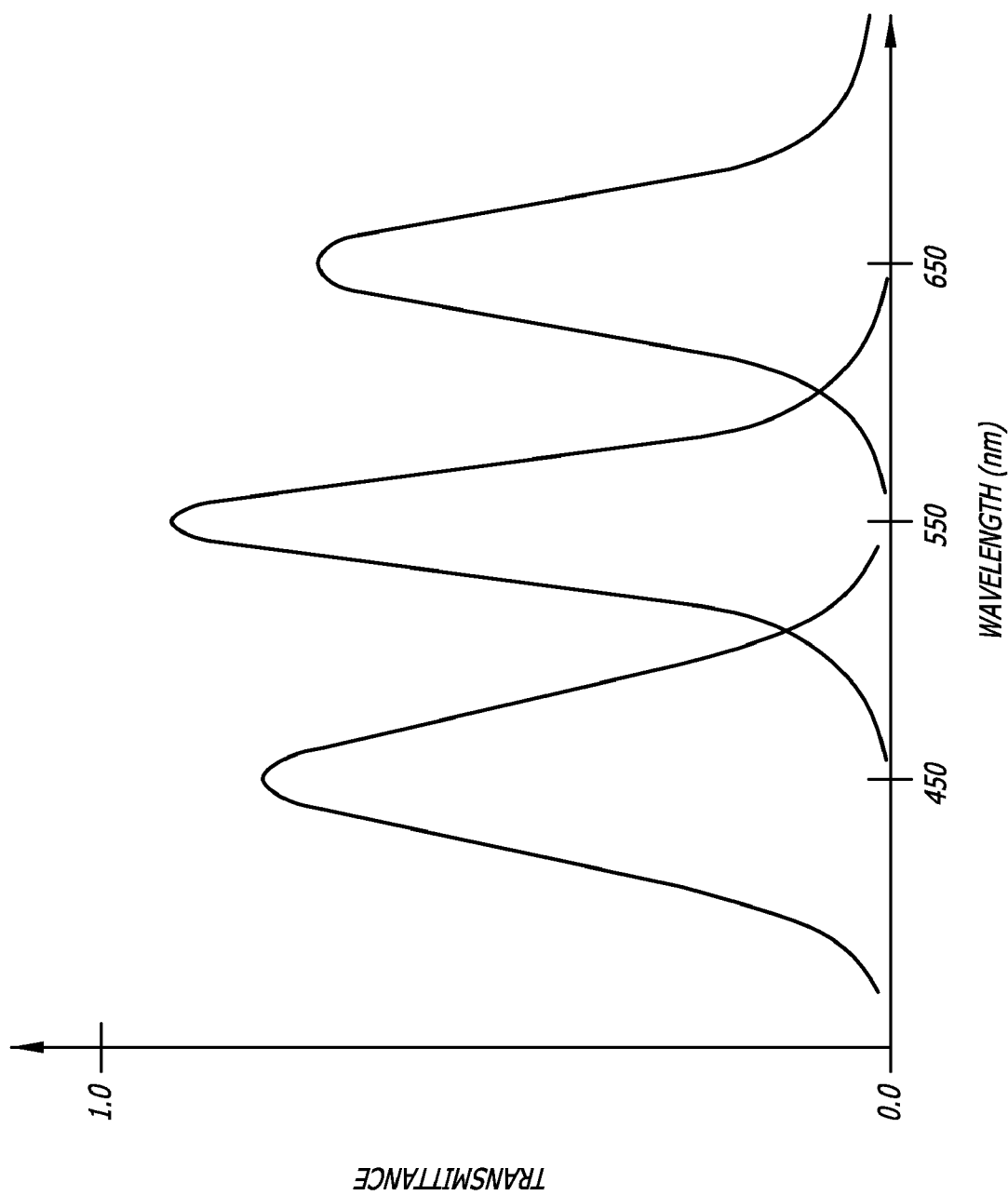
FIG. 3 schematically illustrates the transmission characteristics of an exemplary tunable color filter as a function of wavelength.

FIG. 3 depicts the transmission as a function of wavelength of an exemplary tunable color filter 80. Suitably chosen programming voltages sequentially impressed on filter 80 by circuit 90 yield transmission windows nominally centered at 450 nm, 550 nm, and 650 nm in this example, with the spectral bandwidth of each typically a function of manufacturing parameters such as the thickness of filter 80.

For many ophthalmological examinations it is desirable to image in veridical (true) color, so that an ophthalmologist's visual impressions of retinal images can be used to interpret the presence and onset of subtle retinal pathologies. To provide true-color retinal images, a tunable color filter (such as the line of MicroColor, MacroColor, or VariSpec tunable liquid crystal filters from CRi, Woburn, Mass.) can be employed either before or after the imaging lens to select multiple fundamental wavelength bands. These chromatically differentiated images can then be combined to produce white-balanced veridical chromatic images for direct observation in ambient illumination.

If desired, tunable color filter 80 may be employed in conjunction with imaging optics 30 and image sensor array 40 to produce a sequence of two-dimensional images that may span both visible and infrared wavelengths, depending on the response spectrum of array 40. The resulting hyperspectral image may be used in conjunction with image processing software to produce pseudocolored images that indicate regions of potential pathology, such as regions of enhanced blood flow or pooling, that might warrant more detailed examination.

Tunable color filters are used in both macrophotography and microphotography to obtain exceptional quality images, and are also available in wavelength ranges that span the near and mid-infrared spectral regions. As such, both red-green-blue visible photographs and pseudocolored mixed-visible-IR photographs (or real-time CRT, liquid crystal, or plasma display) images can be produced. This capability allows for examination of the retina in the near and mid infrared spectral regions and provides complementary information in those spectral regions, which can be used to either make or confirm diagnoses of retinal pathologies, or eliminate false positives and false negatives.

Use of a tunable color filter in conjunction with a monochromatic (or grey scale only) image sensor array has several additional advantages. First, the entire image sensor array can be employed in each wavelength band, such that the full resolution of the image sensor array can be achieved, in many cases obviating the need for complex color interpolation algorithms. Second, the wavelength transmission profiles of the filter are programmable, enabling accurate color rendition. Third, the wavelength transmission profiles of filter 80 can be programmably selected to facilitate detection of disease indications or structural features of the eye.

Images read out from the image sensor array may be processed by image processing circuitry and then formatted for display. The system uses image processing to provide for veridical color rendition at the point of display, as judged by the observing ophthalmologist. To this end, the choice of color filters and wavelength bands for exemplary embodiments employing spatially multiplexed color filters, and the choice of wavelength bands and integration time at each wavelength band for exemplary embodiments employing temporally multiplexed color filters may be optimally chosen to provide veridical color for display. In addition, the image processing circuitry can be designed or programmed to modify the color balance as desired to improve the diagnostic impression, structural identification, or pathological distinction by the ophthalmologist.

An image data compression circuit (not shown) may optionally be included in system 10 to reduce the required transmission bandwidth and dissipated power of any of circuits 50, 60, or 90. This image data compression circuit may be located within image sensor array 40, combined with any of circuits 50, 60, or 90, or located in a separate discrete or integrated circuit. The image data compression circuit may be programmable, if desired, with the programming accomplished either manually or in an adaptive manner.

The embodiments described above are illustrative only; other embodiments within the scope of this disclosure will be apparent to those skilled in the art.

The invention claimed is:

1. An ocular imaging system for generating an image of one or more internal structures of a physiologically dilated (non-mydriatic) human eye, including the structure of the retina, the ocular imaging system comprising:

imaging optics, comprising at least one optical element, that is configured to function at least in part as a lens and that is positioned and oriented to form a detectable optical image of the one or more internal structures of the eye, including the retina;

a monochrome image sensor array configured to receive the detectable optical image from the imaging optics and convert it into an electronic image that is representative of the detectable optical image, the image sensor array having a resolution of at least 500 pixels either horizontally or vertically or both and a sensitivity of at least 0.001 lux;

a tunable color filter within the optical path between the eye and the image sensor array, the tunable color filter being configured to allow the central wavelength of its optical bandpass and its dwell time to be controllably set;

a tunable color filter control circuit configured to controllably set the central wavelength and dwell time of the tunable color filter; and an image processing circuit configured to generate a processed electronic image of the one or more internal structures of the eye, including the retina, in veridical color based on two or more electronic images produced by the image sensor array, whereby the image of one or more internal structures of the physiologically dilated (non-mydriatic) human eye, including the retina, has veridical color and is otherwise sufficiently accurate and clear to enable a physician or medical practitioner to diagnose and/or treat the one or more internal structures of the eye, including the retina, without chemical mydriasis (dilation of the pupil of the eye).

2. The ocular imaging system of claim 1, wherein the imaging optics includes at least one element selected from the group consisting of a refractive lens, a gradient index lens, a diffractive lens, a diffractive optical element, and a variable focal length lens.

3. The ocular imaging system of claim 1, wherein the monochrome image sensor array incorporates a fixed pattern color filter.

4. The ocular imaging system of claim 3, wherein the fixed pattern color filter is a Bayer color filter.

5. The ocular imaging system of claim 1, wherein the monochrome image sensor array has a resolution of at least 1,000 pixels either horizontally or vertically or both.

6. The ocular imaging system of claim 1, wherein the monochrome image sensor array has a sensitivity of at least 0.0001 lux.

7. The ocular imaging system of claim 1, wherein the ocular imaging system is configured to generate the image under environmental lighting of illuminance no more than 1 lux without chemical mydriasis (dilation of the pupil).

8. An ocular imaging system for generating an image of one or more internal structures of a physiologically dilated (non-mydriatic) human eye, including the structure of the retina, the ocular imaging system comprising:

imaging optics, comprising at least one optical element, that is configured to function at least in part as a lens and that is positioned and oriented to form a detectable optical image of the one or more internal structures of the eye, including the retina;

a monochrome image sensor array configured to receive the detectable optical image from the imaging optics and convert it into an electronic image that is representative of the detectable optical image, the image sensor array having a resolution of at least 500 pixels either horizontally or vertically or both and a sensitivity of at least 0.001 lux;

a tunable color filter within the optical path between the eye and the image sensor array, the tunable color filter being configured to allow the central wavelength of its optical bandpass and its dwell time to be controllably set;

a tunable color filter control circuit configured to controllably set the central wavelength and dwell time of the tunable color filter; and an image processing circuit configured to generate a processed electronic image of the one or more internal structures of the eye, including the retina, that is pseudocolored based on one or more electronic images produced by the image sensor array, whereby the image of one or more internal structures of the physiologically dilated (non-mydriatic) human eye, including the retina, is pseudocolored, and is otherwise sufficiently accurate and clear to enable a physician or medical practitioner to diagnose and/or treat the internal structures of the eye, including the retina, without chemical mydriasis (dilation of the pupil of the eye).

9. The ocular imaging system of claim 8, wherein the imaging optics includes at least one element selected from the group consisting of a refractive lens, a gradient index lens, a diffractive lens, a diffractive optical element, and a variable focal length lens.

10. The ocular imaging system of claim 8, wherein the monochrome image sensor array incorporates a fixed pattern color filter.

11. The ocular imaging system of claim 10, wherein the fixed pattern color filter is a Bayer color filter.

12. The ocular imaging system of claim 8, wherein the monochrome image sensor array has a resolution of at least 1,000 pixels either horizontally or vertically or both.

13. The ocular imaging system of claim 8, wherein the monochrome image sensor array has a sensitivity of at least 0.0001 lux.

14. The ocular imaging system of claim 8, wherein the tunable color filter control circuit is configured to controllably set the central wavelength of the tunable color filter to a wavelength in the infrared, in order to generate a corresponding electronic image of the one or more internal structures of the eye, including the retina, produced by the image sensor array.

15. The ocular imaging system of claim 8, wherein the tunable color filter control circuit is configured to controllably set several central wavelengths and dwell times of the tunable color filter in succession, in order to generate a hyperspectral image comprising several corresponding electronic images of the one or more internal structures of the eye, including the retina, produced by the image sensor array.

16. The ocular imaging system of claim 8, wherein the tunable color filter control circuit is configured to controllably set several central wavelengths and dwell times of the tunable color filter in succession, including wavelengths in the infrared, in order to generate a hyperspectral image comprising several corresponding electronic images of the one or more internal structures of the eye, including the retina, produced by the image sensor array.

17. The ocular imaging system of claim 8, wherein the ocular imaging system is configured to generate the image under environmental lighting of illuminance no more than 1 lux without chemical mydriasis (dilation of the pupil).

18. A method for generating an image of one or more internal structures of a physiologically dilated (non-mydriatic) human eye of a patient, including the structure of the retina, that has either veridical color or pseudocolor, and that is otherwise sufficiently accurate and clear to enable a physician or medical practitioner to diagnose and/or treat the one or more internal structures of the eye, including the retina, without chemical mydriasis (dilation of the pupil of the eye), comprising the steps of:

placing a patient in a room under light conditions low enough to cause physiological dilation of the patient's eye without resort to chemical dilation;

using imaging optics, including at least one optical element, that is configured to function at least in part as a lens, to form a detectable optical image of the one or more internal structures of the eye;

using a monochrome image sensor array to receive the detectable optical image from the imaging optics and convert it into an electronic image that is representative of the detectable optical image, the image sensor array having a resolution of at least 500 pixels either horizontally or vertically or both and a sensitivity of at least 0.001 lux;

using a tunable color filter to filter the optical path between the eye and the image sensor array, the tunable color filter being configured to allow the central wavelength of its optical bandpass and its dwell time to be controllably set;

using a tunable color filter control circuit configured to controllably set the central wavelength and dwell time of the tunable color filter;

using an image processing circuit to generate one or more processed electronic images of the one or more internal structures of the eye based on one or more electronic images produced by the image sensor array;

setting one or more central wavelengths and one or more dwell times of the tunable color filter control circuit, in view of the illumination conditions and the image sensor array sensitivity, to settings that cause the one or more processed electronic images of the one or more internal structures of the eye to be in either veridical color or pseudocolor; and diagnosing and/or treating the one or more internal structures of the eye based on the processed images, without chemical mydriasis (dilation of the pupil of the eye).

19. The method for using an ocular imaging system of claim 18, wherein the imaging optics includes at least one element selected from the group consisting of a refractive lens, a gradient index lens, a diffractive lens, a diffractive optical element, and a variable focal length lens.

20. The method for using an ocular imaging system of claim 18, wherein the monochrome image sensor array incorporates a fixed pattern color filter.

21. The method for using an ocular imaging system of claim 20, wherein the fixed pattern color filter is a Bayer color filter.

22. The method for using an ocular imaging system of claim 18, wherein the monochrome image sensor array has a resolution of at least 1,000 pixels horizontally or vertically or both.

23. The method for using an ocular imaging system of claim 18, wherein the monochrome image sensor array has a sensitivity of at least 0.0001 lux.

24. The method for using an ocular imaging system of claim 18, wherein the tunable color filter control circuit is configured to controllably set the central wavelength of the tunable color filter to a wavelength in the infrared, in order to generate a corresponding electronic image of the one or more internal structures of the eye, including the retina, produced by the image sensor array.

25. The method for using an ocular imaging system of claim 18, wherein the tunable color filter control circuit is configured to controllably set several central wavelengths and dwell times of the tunable color filter in succession, in order to generate a hyperspectral image comprising several corresponding electronic images of the one or more internal structures of the eye, including the retina, produced by the image sensor array.

26. The method for using an ocular imaging system of claim 18, wherein the tunable color filter control circuit is configured to controllably set several central wavelengths and dwell times of the tunable color filter in succession, including wavelengths in the infrared, in order to generate a hyperspectral image comprising several corresponding electronic images of the one or more internal structures of the eye, including the retina, produced by the image sensor array.

27. The method for using an ocular imaging system of claim 18, wherein the ocular imaging system is capable of generating an image of the one or more internal structures of the eye, including the retina, in a physiologically dilated (non-mydriatic) eye of a human, that has veridical color or pseudocolor and that is otherwise sufficiently accurate and clear to enable a physician or medical practitioner to diagnose and/or treat the one or more internal structures of the eye and retina under environmental lighting of illuminance no more than 1 lux without chemical mydriasis (dilation of the pupil).

* * * * *